United States Patent
Kaneko et al.

(10) Patent No.: US 7,354,615 B2
(45) Date of Patent: Apr. 8, 2008

(54) METHOD FOR PRODUCING MIXED CRYSTAL OF DISODIUM 5'-GUANYLATE AND DISODIUM 5'-INOSINATE

(75) Inventors: Toyokazu Kaneko, Kawasaki (JP); Yasuo Yonou, Kawasaki (JP); Naoto Hirano, Kawasaki (JP); Shigemitsu Abe, Kawasaki (JP); Kunihiko Toumori, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 598 days.

(21) Appl. No.: 10/481,893

(22) PCT Filed: Jul. 19, 2002

(86) PCT No.: PCT/JP02/07345

§ 371 (c)(1),
(2), (4) Date: Jan. 5, 2004

(87) PCT Pub. No.: WO03/011886

PCT Pub. Date: Feb. 13, 2003

(65) Prior Publication Data

US 2004/0180909 A1   Sep. 16, 2004

(30) Foreign Application Priority Data

Jul. 26, 2001   (JP)   ............... 2001-225445

(51) Int. Cl.
*A23L 1/221*   (2006.01)
*B01D 9/00*   (2006.01)

(52) U.S. Cl. ............... 426/650; 426/425; 23/295 R

(58) Field of Classification Search ............... 426/425, 426/429, 431, 650; 23/295 R, 299, 300
See application file for complete search history.

(56) References Cited

U.S. PATENT DOCUMENTS 6,821,306 B2 * 11/2004 Tachibana et al. ........ 23/295 R

FOREIGN PATENT DOCUMENTS

| DE | 17 95 649 | 2/1973 |
|----|-----------|--------|
| JP | 40-12914  | 6/1965 |
| JP | 46-15668  | 4/1971 |
| JP | 47-16783  | 5/1972 |
| JP | 50-160295 | 12/1975 |
| JP | 53 124686 | 10/1978 |
| JP | 3-223299  | 10/1991 |

* cited by examiner

*Primary Examiner*—Leslie Wong
(74) *Attorney, Agent, or Firm*—Oblon, Spivak, McClelland, Maier & Neustadt, P.C.

(57) ABSTRACT

Disclosed herein are a process for producing mixed crystals of disodium 5'-guanylate and disodium 5'-inosinate which comprises precipitating mixed crystals of disodium 5'-guanylate and disodium 5'-inosinate (I+G mixed crystals) by adding an aqueous mixed solution of disodium 5'-guanylate and disodium 5'-inosinate and a hydrophilic organic solvent at the same time into a crystallization vessel in such manner that the ratio of the hydrophilic organic solvent to the liquid phase in the crystallization vessel is maintained in a range of 30 to 70 vol %, as well as such process for producing I+G mixed crystals wherein said producing of I+G mixed crystals is carried out by seeding crystallization wherein crystals of 5'-IMP2Na or/and I+G mixed crystals are used as seed crystals. According to these production processes, the by-production of amorphous solids of 5'-GMP2Na which adversely affect separability of the crystals concerned, is inhibited, and therefore, such mixed crystals having a good separability without contamination of such amorphous solids, can be produced in a high productivity.

12 Claims, No Drawings

US 7,354,615 B2

METHOD FOR PRODUCING MIXED CRYSTAL OF DISODIUM 5'-GUANYLATE AND DISODIUM 5'-INOSINATE

This application is a 371 of PCT/JP02/07345 filed Jul. 19, 2002.

TECHNICAL FIELD

The present invention relates to a process for producing both of disodium 5'-guanylate (hereinafter, referred to as 5'-GMP2Na or only GMP) and disodium 5'-inosinate (hereinafter, referred to as 5'-IMP2Na or only IMP), which are important as seasonings, medicaments, and the like, in the form of not a mere mixture of their respective crystals but mixed crystals thereof.

BACKGROUND

As has been described in the preceding section, 5'-GMP2Na and 5'-IMP2Na are important in the fields of seasonings, medicaments, and the like. However, when it is necessary to use both the compounds in combination, it is extremely difficult to prepare a mixture having a predetermined mixed ratio by the mere mixing of crystals of both the respective compounds owing to the differences in crystal natures and powder properties of the compounds, and also the handling of such a mixture is accompanied by various difficulties.

By the way, as methods for producing 5'-GMP2Na and 5'-IMP2Na in the form of their mixed crystals, the following three methods can be mentioned when roughly classified. That is, (1) a method of dissolving 5'-GMP2Na and 5'-IMP2Na in water, followed by precipitating 5'-GMP2Na and 5'-IMP2Na in the form of mixed crystals thereof (hereinafter, abbreviated as I+G mixed crystals) from the resulting solution by cooling, concentrating, and addition of an alcohol (Japanese Patent Publication Nos. 16582/1979 and 4787/1980), (2) a method of dissolving 5'-GMP2Na and 5'-IMP2Na in an aqueous solution containing a hydrophilic organic solvent such as methanol or the like, followed by obtaining mixed crystals of 5'-GMP2Na and 5'-IMP2Na (i.e., I+G mixed crystals) from the resulting solution, and a crystallization method wherein an organic solvent is added to an aqueous mixed solution of 5'-GMP2Na and 5'-IMP2Na (Japanese Patent Publication No. 12914/1965), and (3) a method wherein an aqueous solution containing 5'-IMP2Na is gradually added to a slurry solution in which 5'-GMP2Na is present as the bottom body (Ger., Bodenkörper), whereby I+G mixed crystals are formed (Japanese Patent Publication No. 215494/1991 and Japanese Patent No. 2770470).

On the other hand, 5'-GMP2Na and 5'-IMP2Na are known to form I+G mixed crystals in an aqueous solution containing a hydrophilic organic solvent such as methanol or in a mere aqueous solution, while 5'-GMP2Na is incorporated into the crystal lattice of 5'-IMP2Na. The X-ray diffraction chart of the mixed crystals shows almost the same pattern as that of 5'-IMP2Na, and it is considered that 5'-GMP2Na having a similar chemical structure to that of 5'-IMP2Na enters the crystal lattice of 5'-IMP2Na, wherein a stable state is maintained by hydrogen bonding. The crystals of 5'-IMP2Na have a good crystal shape, and I+G mixed crystals having the same crystal lattice has almost the same good crystal shape.

At the time when I+G mixed crystals are to be obtained, when according to the above method (1), in order to obtain a product (mixed crystals) having a desirable ratio (weight ratio) of 5'-IMP2Na and 5'-GMP2Na (hereinafter, the ratio (weight ratio) of both the compounds is abbreviated as I/G ratio), it is necessary to control strictly concentrating drain, feed liquid, and setting conditions of temperature, pressure, and the like, in the case of the crystallization by concentrating, and more strict control of the composition of crystallizing liquid is required in the case of the crystallization by cooling, since the composition of crystallizing liquid changes continuously. Thus, there is the problem that apparatuses and process controls concerned get complicated in both cases. According to the method (2), crystallization can be effected in high recovery yields, but when carried out industrially, an expensive explosion-preventing equipment is required because an organic solvent is used, so that there is the disadvantage that the production cost increases. Moreover, it is difficult to control crystallizing conditions, and there is the problem that GMP is generated depending on the crystallizing conditions, and, in turn, the separability of the resulting crystals decreases. According to the method (3), it is necessary to keep separate the raw materials 5'-IMP2Na and 5'-GMP2Na prior to crystallization, and hence the number of equipments increases for avoiding the mixing before crystallization.

DISCLOSURE OF THE INVENTION

Under the background art as described in the preceding section, it is an object of the present invention to provide a method for producing I+G mixed crystals in a high productivity, in which method the by-production of amorphous solids of 5'-GMP2Na which adversely affect the separability of the crystals concerned, is inhibited, and the resulting mixed crystals have a good separability without contamination of such amorphous solids.

As a result of their intensive studies for improving the crystallization methods of I+G mixed crystals, which are hitherto known and require burdensome and complex controls and steps, the present inventors have found that I+G mixed crystals having stable crystal separability and quality can be obtained by crystallization under the condition of a constant solvent concentration which is industrially easy to control, whereby the generation of amorphous solids of 5'-GMP2Na is prevented. Based on these findings, they have accomplished the present invention.

Accordingly, the present invention relates to a process for producing mixed crystals of disodium 5'-guanylate and disodium 5'-inosinate which comprises a step of precipitating mixed crystals of disodium 5'-guanylate and disodium 5'-inosinate by adding an aqueous mixed solution of disodium 5'-guanylate and disodium 5'-inosinate and a hydrophilic organic solvent at the same time into a crystallization vessel in such manner that the ratio of the hydrophilic organic solvent to the liquid phase in the crystallization vessel is maintained in a range of 30 to 70 vol %. It also relates to such process for producing mixed crystals of disodium 5'-guanylate and disodium 5'-inosinate which comprises a further step of adding, as seed crystals, crystals of disodium 5'-inosinate or/and I+G mixed crystals.

In the following will be described the present invention in greater detail.

The aqueous mixed solution of 5'-IMP2Na and 5'-GMP2Na for use according to the present invention can be prepared not only from product crystals of their respective compounds but also from, for example, I+G mixed crystals having an I/G ratio outside a predetermined range or crystals at a crude crystal level in each production process of the two kinds of compounds by a fermentation process, an organic synthesis, or the like. However, the content of impurities is, needless to say, limited to a level where the solubility or crystal growth rate of I+G mixed crystals is not affected. The composition of each compound in the aqueous mixed solution can be determined to be within a range of 5 to 40 wt %, preferably 8 to 25 wt % according to the I/G ratio (weight ratio) of the target I+G mixed crystals. Moreover, the aqueous mixed solution may contain a hydrophilic organic solvent in an amount of 20 vol % or less. Furthermore, for obtaining I+G mixed crystals of an I/G ratio=1.0, the I/G ratio of the mixed solution should be in a range of 0.90 to 0.97.

With regard to the pH upon crystallizing operation, I+G mixed crystals can be obtained when the pH is in the pH range wherein disodium salts of 5'-IMP2Na and 5'-GMP2Na can exist, i.e., in the range of pH 6 to 10, but the pH is desirably from about pH 7 to 8.

As the hydrophilic organic solvent, methanol, ethanol, propanol, isopropanol, or mixtures thereof can be used. Preferably, it is desirable to use methanol since the resulting crystal shape is most suitable for solid-liquid separation. Moreover, the organic solvent to be used may be used after diluting with water, but it is industrially preferred that the concentration range of the solvent is from 80 to 100 vol % since the increase of dilution rate results in the increase of amount of the solvent to be added.

In the case where I+G mixed crystals are crystallized by pouring an aqueous mixed solution of 5'-IMP2Na and 5'-GMP2Na and a hydrophilic organic solvent into a crystallization vessel, followed by mixing them according to the process of the present invention, it is also possible to add, as seed crystals, 5'-IMP2Na crystals or I+G mixed crystals (so-called seeding crystallization). Such seed crystals can be added or used in the form of a powder (microcrystals) or a slurry thereof. The timing of adding seed crystals is desirably within the time range wherein the hydrophilic organic solvent is added in an amount of 20% or less of the total amount. The amount of seed crystals to be used for obtaining crystals suitable for solid-liquid separation, is desirably in an amount of about 0.1 to 10 wt %, preferably about 1 to 5 wt %, of the total amount of the 5'-IMP2Na and 5'-GMP2Na in the aqueous mixed solution. Addition of seed crystals brings about the effect that specific volumes which are one of the physical properties of powder are lowered.

At the time when an aqueous mixed solution of 5'-IMP2Na and 5'-GMP2Na and a hydrophilic organic solvent are added into a crystallization vessel at the same time, it is necessary to place the solvent alone or a mixed solution of an aqueous mixed solution of 5'-IMP2Na and 5'-GMP2Na and a hydrophilic organic solvent in the crystallization vessel in such an amount that the content therein can be stirred. Furthermore, the stirring should be maintained in such good state that the solvent may rapidly diffuse, whereby the solvent can be mixed with the aqueous mixed solution rapidly and homogeneously. Moreover, in order to maintain the I+G mixed crystals in a good crystal shape, the stirring is desirably carried out at the lowest speed as far as possible, and preferably SV=0.3 to 0.6 is desirable.

The temperature during the addition at the same time may be set at 20 to 50° C., but preferably, it is desirable to carry out the operation at 40±5° C. Moreover, during the addition at the same time, the temperature may be changed, for example, by a cooling operation.

After the addition at the same time, it is possible to conduct immediately solid-liquid separation without any further operation, but it is also possible to conduct further addition of a small amount of the hydrophilic organic solvent or a cooling operation in order to improve the yield. The ratio (concentration) of the organic solvent to the liquid phase in the crystallization system may be in a range of 30 to 70 vol %, but industrially, 60 vol % or more is preferred for ensuring the yield.

BEST MODE FOR CARRYING OUT THE INVENTION

In the following will be given some concrete embodiments of the present invention.

COMPARATIVE EXAMPLE 1

436.0 g of an aqueous solution containing 44.7 g of 5'-IMP2Na and 45.6 g of 5'-GMP2Na was kept at a temperature of 40° C., and 867 ml of aqueous 95 vol % methanol solution was added thereto over a period of 5 hours. The final methanol concentration at that time was 65 vol %. After the addition, the whole mass was cooled to 10° C. over a period of 7 hours. Amorphous solids of 5'-GMP2Na were generated at 10 to 20° C. in the course of cooling.

EXAMPLE 1

200 ml of aqueous 30 vol % methanol solution was placed in a crystallization vessel and kept at a temperature of 40° C. Thereto were added 872.0 g of an aqueous solution containing 89.5 g of 5'-IMP2Na and 91.1 g of 5'-GMP2Na and aqueous 95 vol % methanol solution at the same time over a period of 5 hours. During the addition at the same time, the addition was conducted in such that the methanol concentration in the crystallization vessel was maintained to be 30 vol %.

After the addition, the whole mass was cooled to 10° C., but no precipitation of amorphous solids of 5'-GMP2Na was confirmed.

EXAMPLE 2

200 ml of aqueous 35 vol % methanol solution was placed in a crystallization vessel and kept at a temperature of 40° C. Thereto were added 872.0 g of an aqueous solution containing 89.5 g of 5'-IMP2Na and 91.1 g of 5'-GMP2Na and aqueous 95 vol % methanol solution at the same time over a period of 3 hours. During the addition at the same time, the addition was controlled in such that the methanol concentration of the liquid phase in the crystallization vessel was maintained to be 30 vol %.

After the addition, the whole mass was cooled to 10° C., but no precipitation of amorphous solids of 5'-GMP2Na was confirmed.

EXAMPLE 3

175 ml of aqueous 45 vol % methanol solution was placed in a crystallization vessel and kept at a temperature of 40° C. Thereto were added 763.0 g of an aqueous solution containing 78.3 g of 5'-IMP2Na and 79.2 g of 5'-GMP2Na and aqueous 95 vol % methanol solution at the same time over a period of 3 hours. During the addition at the same time, the addition was controlled in such that the methanol concentration of the liquid phase in the crystallization vessel was maintained to be 45 vol %.

After the addition, the whole mass was cooled to 10° C., but no precipitation of amorphous solids of 5'-GMP2Na was confirmed.

EXAMPLE 4

175 ml of aqueous 65 vol % methanol solution was placed in a crystallization vessel and kept at a temperature of 40° C. Thereto were added 817.5 g of an aqueous solution containing 83.9 g of 5'-IMP2Na and 85.4 g of 5'-GMP2Na and aqueous 95 vol % methanol solution at the same time over a period of 3 hours. During the addition at the same time, the addition was controlled in such that the methanol concentration of the liquid phase in the crystallization vessel was maintained to be 65 vol %.

After the addition, the whole mass was cooled to 10° C., but no precipitation of amorphous solids of 5'-GMP2Na was confirmed.

EXAMPLE 5

175 ml of aqueous 45 vol % methanol solution was placed in a crystallization vessel and kept at a temperature of 40° C. Thereto was added 6.3 g of I+G mixed crystals as seed crystals. To the resulting slurry were added 763.0 g of an aqueous solution containing 78.3 g of 5'-IMP2Na and 79.2 g of 5'-GMP2Na and aqueous 95 vol % methanol solution at the same time over a period of 3 hours. During the addition at the same time, the addition was controlled in such that the methanol concentration of the liquid phase in the crystallization vessel was maintained to be 45 vol %.

After the addition, the whole mass was cooled to 10° C., but no precipitation of amorphous solids of 5'-GMP2Na was confirmed.

EXAMPLE 6

175 ml of aqueous 45 vol % methanol solution was placed in a crystallization vessel and kept at a temperature of 40° C. Thereto was added, as seed crystals, a slurry of 6.3 g of I+G mixed crystals suspended in an aqueous 45 vol % methanol solution (reslurried). To the resulting slurry were added 963.0 g of an aqueous solution containing 78.3 g of 5'-IMP2Na and 79.2 g of 5'-GMP2Na and aqueous 95 vol % methanol solution at the same time over a period of 3 hours. During the addition at the same time, the addition was controlled in such that the methanol concentration of the liquid phase in the crystallization vessel was maintained to be 45 vol %.

After the addition, the whole mass was cooled to 10° C., but no precipitation of amorphous solids of 5'-GMP2Na was confirmed.

It was confirmed from the foregoing that the precipitation of amorphous solids of 5'-GMP2Na can be avoided according to the process of the present invention.

Analytical Results

On the crystals obtained in Comparative Example 1 and Examples 1 to 6, their respective contents and I/G ratio of the 5'-IMP2Na and the 5'-GMP2Na, and rough specific volumes were measured. The results will be shown below in Table 1. Moreover, on the mother liquor after separated, the respective concentrations of 5'-IMP2Na and 5'-GMP2Na were measured and, based on the results, the I/G ratio of the mother liquor and the crystallization yield of the I+G mixed crystals were determined. The results will be shown below in Table 2.

Incidentally, the respective contents of the 5'-IMP2Na and the 5'-GMP2Na in the various mixed crystals obtained were determined by HPLC, and the respective rough specific volumes of the mixed crystals obtained were measured with a bulk density tester manufactured by Kuramochi kagaku Co., Ltd. Moreover, regarding the separated mother liquors, the respective concentrations of the 5'-IMP2Na and the 5'-GMP2Na were measured by HPLC.

All the I/G ratios of the I+G mixed crystals were found to be about 1. With regard to the rough specific volume which is an index of physical properties of powder, lowered values were observed, and therefore, desirable results were obtained in accordance with the crystallization method of the present invention, as compared with Comparative Example 1. And, in the cases where seed crystals were used (Examples 5 and 6), the rough specific volumes were further lowered, and therefore, more desirable results were obtained.

Furthermore, regarding the I/G ratios of the mother liquors, they were increased, as the concentrations at simultaneous addition were increased. All the yields were of almost the same level.

TABLE 1

Analytical Results of Crystals

| | Contents in Crystals (wt %) | | I/G Ratio | Rough Specific Volume |
|---|---|---|---|---|
| | IMP | GMP | | |
| Example | | | | |
| 1 | 50.81 | 48.79 | 1.04 | 1.66 |
| 2 | 51.68 | 50.21 | 1.03 | 1.72 |
| 3 | 50.87 | 49.93 | 1.02 | 1.75 |
| 4 | 53.95 | 51.91 | 1.04 | 1.67 |
| 5 | 52.85 | 51.06 | 1.04 | 1.54 |
| 6 | 51.15 | 49.32 | 1.04 | 1.52 |
| Comparative Example 1 | 52.70 | 47.60 | 1.04 | 1.87 |

TABLE 2

Analytical Results of Mother Liquors

| | Concentration in Mother Liquous (wt %) | | I/G Ratio | Crystallization Yield (%) |
|---|---|---|---|---|
| | IMP | GMP | | |
| Example | | | | |
| 1 | 0.132 | 0.882 | 0.150 | 95.1 |
| 2 | 0.143 | 0.819 | 0.175 | 95.4 |
| 3 | 0.155 | 0.794 | 0.195 | 95.4 |
| 4 | 0.192 | 0.762 | 0.252 | 95.3 |
| 5 | 0.153 | 0.789 | 0.194 | 95.2 |
| 6 | 0.157 | 0.790 | 0.199 | 95.5 |
| Comparative Example 1 | 0.134 | 0.820 | 0.163 | 95.4 |

INDUSTRIAL APPLICABILITY

Upon crystallization of I+G mixed crystals from a mixed solution of 5'-IMP2Na and the 5'-GMP2Na with the use of an organic solvent and with or without the use of 5'-IMP2Na crystals or I+G mixed crystals as seed crystals, precipitation of 5'-GMP-2Na can be prevented when in accordance with the present invention. Moreover, if in accordance with the present invention, rough specific volumes which are an index of the physical properties of powder get smaller, as compared with the prior art technology.

The invention claimed is:

1. A process for producing mixed crystals of disodium 5'-guanylate and disodium 5'-inosinate, wherein said process comprises precipitating mixed crystals of disodium 5'-guanylate and disodium 5'-inosinate by simultaneously adding a hydrophilic organic solvent and an aqueous mixed solution of disodium 5'-guanylate and disodium 5'-inosinate into a crystallization vessel to produce mixed crystals of disodium 5'-guanylate and disodium 5'-inosinate in a liquid phase, wherein said simultaneously adding is carried out in a manner such that a volumetric concentration of said hydrophilic organic solvent to said liquid phase in said crystallization vessel is maintained in a range of 30-70 vol. %.

2. The process for producing mixed crystals of disodium 5'-guanylate and disodium 5'-inosinate according to claim 1, wherein said precipitating mixed crystals of disodium 5'-guanylate and disodium 5'-inosinate is carried out in the presence of seed crystals, wherein said seed crystals are selected from the group consisting of disodium 5'-inosinate seed crystals and mixed crystals of disodium 5'-guanylate and disodium 5'-inosinate.

3. The process for producing mixed crystals of disodium 5'-guanylate and disodium 5'-inosinate according to claim 1, wherein said hydrophilic organic solvent is selected from the group consisting of methanol, ethanol, propanol, isopropanol, and mixtures thereof.

4. The process for producing mixed crystals of disodium 5'-guanylate and disodium 5'-inosinate according to claim 1, wherein said hydrophilic organic solvent is methanol.

5. The process for producing mixed crystals of disodium 5'-guanylate and disodium 5'-inosinate according to claim 1, wherein the volumetric concentration of said hydrophilic organic solvent to said liquid phase in said crystallization vessel is maintained in a range of 60-70 vol. %.

6. The process for producing mixed crystals of disodium 5'-guanylate and disodium 5'-inosinate according to claim 1, wherein said precipitating mixed crystals of disodium 5'-guanylate and disodium 5'-inosinate is carried out at a pH ranging from 6 to 10.

7. The process for producing mixed crystals of disodium 5'-guanylate and disodium 5'-inosinate according to claim 1, wherein said precipitating mixed crystals of disodium 5'-guanylate and disodium 5'-inosinate is carried out at a pH ranging from 7 to 8.

8. The process for producing mixed crystals of disodium 5'-guanylate and disodium 5'-inosinate according to claim 1, wherein said precipitating mixed crystals of disodium 5'-guanylate and disodium 5'-inosinate is carried out at a temperature of 20-50° C.

9. The process for producing mixed crystals of disodium 5'-guanylate and disodium 5'-inosinate according to claim 1, wherein said precipitating mixed crystals of disodium 5'-guanylate and disodium 5'-inosinate is carried out at a temperature of 35-45° C.

10. The process for producing mixed crystals of disodium 5'-guanylate and disodium 5'-inosinate according to claim 1, wherein the ratio of disodium 5'-inosinate to disodium 5'-guanylate within the mixed crystals of disodium 5'-guanylate and disodium 5'-inosinate is about 1.

11. The process for producing mixed crystals of disodium 5'-guanylate and disodium 5'-inosinate according to claim 1, wherein the ratio of disodium 5'-inosinate to disodium 5'-guanylate within the mixed crystals of disodium 5'-guanylate and disodium 5'-inosinate is from 1.02 to 1.04.

12. The process for producing mixed crystals of disodium 5'-guanylate and disodium 5'-inosinate according to claim 1, wherein said process inhibits the generation of amorphous solids of 5'-GMP2Na.

* * * * *